United States Patent
Kahn et al.

(10) Patent No.: US 9,459,597 B2
(45) Date of Patent: Oct. 4, 2016

(54) METHOD AND APPARATUS TO PROVIDE AN IMPROVED SLEEP EXPERIENCE BY SELECTING AN OPTIMAL NEXT SLEEP STATE FOR A USER

(71) Applicants: Philippe Kahn, Santa Cruz, CA (US); Arthur Kinsolving, Santa Cruz, CA (US)

(72) Inventors: Philippe Kahn, Santa Cruz, CA (US); Arthur Kinsolving, Santa Cruz, CA (US)

(73) Assignee: DPTechnologies, Inc., Scotts Valley, CA (US)

( * ) Notice: Subject to any disclaimer, the term of this patent is extended or adjusted under 35 U.S.C. 154(b) by 116 days.

(21) Appl. No.: 13/781,742

(22) Filed: Feb. 28, 2013

(65) Prior Publication Data

US 2013/0234823 A1 Sep. 12, 2013

Related U.S. Application Data

(60) Provisional application No. 61/607,530, filed on Mar. 6, 2012.

(51) Int. Cl.
*G08B 21/00* (2006.01)
*G05B 13/00* (2006.01)
*A61M 21/02* (2006.01)
(Continued)

(52) U.S. Cl.
CPC ............ *G05B 13/00* (2013.01); *A61M 21/02* (2013.01); *G06F 19/3406* (2013.01); *G06F 19/3481* (2013.01); *A61M 2021/0016* (2013.01); *A61M 2021/0027* (2013.01); *A61M 2021/0044* (2013.01); *A61M 2205/332* (2013.01); *A61M 2205/3553* (2013.01); *A61M 2205/3584* (2013.01); *A61M 2205/3592* (2013.01); *A61M 2230/06* (2013.01); *A61M 2230/30* (2013.01); *A61M 2230/63* (2013.01)

(58) Field of Classification Search
CPC ... A61M 21/02; G05B 13/00; G06F 19/3406
USPC .......................... 340/3.1, 573.1, 575, 286.07; 600/26–28, 301
See application file for complete search history.

(56) References Cited

U.S. PATENT DOCUMENTS

| 4,573,804 A | 3/1986 | Kavoussi et al. |
| 4,858,609 A | 8/1989 | Cole |

(Continued)

FOREIGN PATENT DOCUMENTS

| AU | 2003203967 | 11/2004 |
| DE | 19642316 A1 | 4/1998 |

(Continued)

OTHER PUBLICATIONS

Jaines, Kira, "Music to Help You Fall Sleep," <http://www.livestrong.com/article/119802-music-fall-sleep/>, May 10, 2010, 2 pages.

(Continued)

*Primary Examiner* — Mark Rushing
(74) *Attorney, Agent, or Firm* — HIPLegal LLP; Judith Szepesi (57) ABSTRACT

A sleep sensing system comprising a sensor to obtain real-time information about a user, a sleep state logic to determine the user's current sleep state based on the real-time information. The system further comprising a sleep stage selector to select an optimal next sleep state for the user, and a sound output system to output sounds to guide the user from the current sleep state to the optimal next sleep state.

20 Claims, 8 Drawing Sheets

(51) Int. Cl.
*G06F 19/00* (2011.01)
*A61M 21/00* (2006.01)

(56) References Cited

U.S. PATENT DOCUMENTS

| | | | |
|---|---|---|---|
| 5,008,865 | A | 4/1991 | Shaffer et al. |
| 5,335,657 | A | 8/1994 | Terry, Jr. et al. |
| 5,545,192 | A | 8/1996 | Czeisler et al. |
| 5,928,133 | A | 7/1999 | Halyak |
| 6,239,706 | B1 * | 5/2001 | Yoshiike et al. ........... 340/573.4 |
| 6,350,275 | B1 | 2/2002 | Vreman et al. |
| 6,963,271 | B1 | 11/2005 | Fyffe |
| 7,106,662 | B1 | 9/2006 | Acker |
| 7,280,439 | B1 | 10/2007 | Shaddox |
| 8,179,270 | B2 | 5/2012 | Rai et al. |
| 8,398,546 | B2 | 3/2013 | Pacione et al. |
| 2002/0080035 | A1 | 6/2002 | Youdenko |
| 2003/0095476 | A1 | 5/2003 | Mollicone et al. |
| 2003/0231495 | A1 * | 12/2003 | Searfoss, III ................ 362/251 |
| 2005/0012622 | A1 | 1/2005 | Sutton |
| 2005/0143617 | A1 | 6/2005 | Auphan |
| 2005/0154330 | A1 | 7/2005 | Loree |
| 2005/0190065 | A1 | 9/2005 | Ronnholm |
| 2006/0136018 | A1 | 6/2006 | Lack |
| 2006/0293608 | A1 | 12/2006 | Rothman et al. |
| 2007/0287930 | A1 | 12/2007 | Sutton |
| 2008/0191885 | A1 | 8/2008 | Loree, IV et al. |
| 2008/0234785 | A1 | 9/2008 | Nakayama et al. |
| 2009/0105785 | A1 | 4/2009 | Wei et al. |
| 2010/0079294 | A1 | 4/2010 | Rai et al. |
| 2010/0083968 | A1 | 4/2010 | Wondka et al. |
| 2010/0102971 | A1 | 4/2010 | Virtanen et al. |
| 2011/0160619 | A1 | 6/2011 | Gabara |
| 2011/0230790 | A1 | 9/2011 | Kozlov |
| 2011/0295083 | A1 | 12/2011 | Doelling et al. |
| 2012/0253220 | A1 | 10/2012 | Rai et al. |
| 2013/0018284 | A1 | 1/2013 | Kahn et al. |
| 2013/0060306 | A1 * | 3/2013 | Colbauch ....................... 607/88 |
| 2014/0051938 | A1 * | 2/2014 | Goldstein et al. ............ 600/301 |
| 2014/0207292 | A1 | 7/2014 | Ramagem et al. |
| 2015/0148871 | A1 | 5/2015 | Maxik et al. |
| 2015/0190086 | A1 | 7/2015 | Chan et al. |

FOREIGN PATENT DOCUMENTS

| | | |
|---|---|---|
| EP | 1139187 B1 | 10/2001 |
| WO | WO 2011/141840 | 11/2011 |

OTHER PUBLICATIONS

Sound-Remedies.com: Sonic Solutions for Health, Learning & Productivity, <http://www.sound-remedies.com/ammusforslee. html>, Accessed May 23, 2013, 2 pages.
PCT/US2013/028939, International Search Report and Written Opinion, Date of Mailing May 10, 2013, 10 pages.
"Power Nap," <en.wikipedia.org/wiki/Power.sub.—nap>, Last Modified Sep. 20, 2012, 4 pages.
"Slow Wave Sleep," <en.wikipedia.org/wiki/Slow-wave.sub.—sleep>, Last Modified Jul. 22, 2012, 4 pages.
Patel, et al., Validation of Basis Science Advanced Sleep Analysis, Estimation of Sleep Stages and Sleep Duration, Basis Science, San Francisco, CA, Jan. 2014, 6 pages.

* cited by examiner

METHOD AND APPARATUS TO PROVIDE AN IMPROVED SLEEP EXPERIENCE BY SELECTING AN OPTIMAL NEXT SLEEP STATE FOR A USER

RELATED CASES

The present invention claims priority to U.S. Provisional Patent Application No. 61/607,530, filed on Mar. 6, 2012. The provisional patent application is incorporated herein by reference.

FIELD

The present invention relates to sleep, and more particularly to improving the sleep experience.

BACKGROUND

Numerous types of white noise, nature noise, or music devices are available which are sold to help users sleep better. In general, these devices provide music or other sounds on a timer, helping the user fall asleep with the sounds. The sound can be used to block out background sounds. In some systems, the selected sounds are calming, such as rain or waves.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A method and apparatus to provide conditions to guide a user into an optimal sleep patterns. In one embodiment, the system includes a physiological monitor that may be used to detect a user's current sleep state. The system is further able to determine environmental factors, which may include a current time, alarm settings, temperature, barometric pressure, weather, and other factors that may impact the user's optimal sleep experience. Furthermore, in one embodiment, the system may utilize a known waking time, to ensure that the user sleeps well and wakes up refreshed. In one embodiment the system may control conditions such as sounds, odors (olfactory), tactile outputs (haptics), environmental conditions (temperature, humidity, light), mattress firmness, and other environmental conditions which would improve the user's sleep quality. In one embodiment, the system may interface with a house automation system, to control some of these conditions.

For example, the system may use music or other sound patterns to guide the user into a deep sleep. In one embodiment, other conditions may also be adjusted to guide the user to the appropriate sleep state. In one embodiment, the system may guide the user back into deep sleep as needed, throughout the sleep period. The system may further adjust conditions to gradually wake the person at the perfect time, to complete the optimal sleep pattern. In one embodiment, the waking conditions may be designed to refresh, and energize the user. In one embodiment the time to wake up a user may be selected based on a number of factors, including sleep phase, calendar data, and weather and traffic data. For example, a user may set an alarm to "before 7:30 a.m." to make an appointment at 9 a.m. However, if the system has information indicating that it is snowing, the system may wake up the user prior to that time.

The following detailed description of embodiments of the invention make reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

Figure 1:
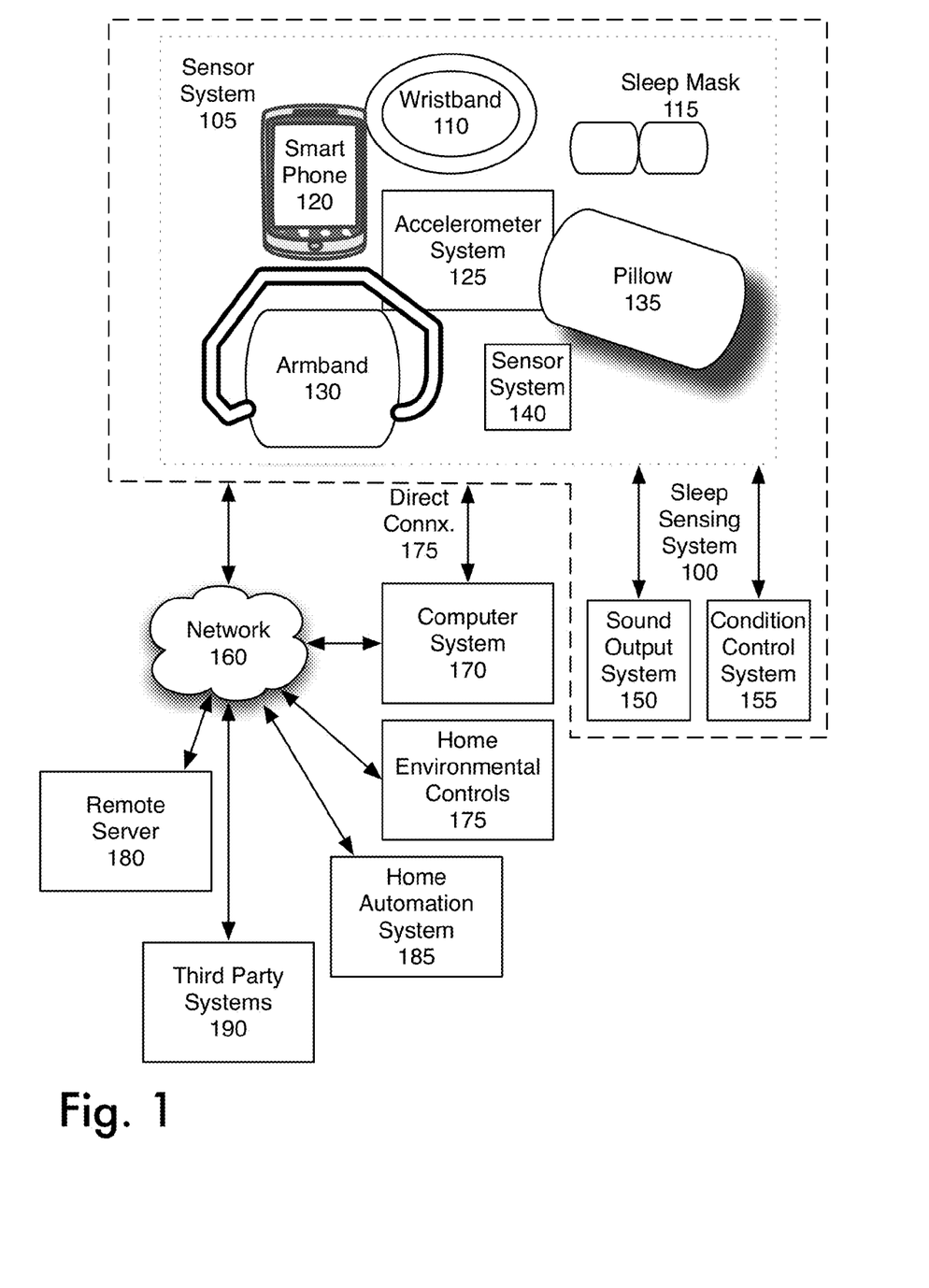
FIG. 1 is a network diagram showing one embodiment a system.

FIG. 1 is a network diagram showing one embodiment a system. The system, in one embodiment, includes a sleep sensing system 100. The sleep sensing system 100 includes sensor system 105. The sensor system 105 may be embodied in a body-worn device such as a wristband 110 or sleep mask 115, or a human carried device such as a smart phone 120 or accelerometer system 125. In one embodiment, the sensor system 105 may be implemented in a sleep-only device such as an armband 130 or pillow 135.

The sleep sensing system 100 further includes a sound output system 150. The sound output system 150 may be implemented in the same device as the sensor system 105, such as a speaker integrated into the wristband 110, smart phone 120, pillow 135, or other sensing system 140. Alternatively, the sound output system 150 may be a separate device, such as a speaker system, a pillow 135 that includes a speaker, etc. The sound output system 150 is used to guide the user to an improved sleep pattern, as will be described in more detail below. The sound output system 150 communicates with the sensor system 105, which controls the sound output system 150 to generate sounds based on the real time data obtained by the sensors.

In one embodiment, in addition to outputting the sound output system 150, the system may include other output mechanisms, such as tactile output, that are useful to transition a user to a different sleep phase. For example, in one embodiment, the sleep sensing system 100 may include condition control system 155, to control the conditions other than sound in the environment.

In one embodiment, the condition control system 155 enables the sleep sensing system 100 to have access to home environmental controls 175. Home environmental controls 175 may interface with a home automation system 185. In one embodiment, one or more (temperature, light, humidity, mattress firmness). In one embodiment, the system interfaces with a home automation system 175, so it is able to open/close windows, adjust thermostats, humidity, mattress controls, lighting, olfactory stimulants (odors) etc.

In one embodiment, the sensor system 105 is located in a wristband 110 or armband 130, and the sound output system 150 is a smart phone 120 or pillow 135, while the condition control system 155 is a communication logic that enables the sleep sensing system 100 to communicate with home environmental controls 175 and/or home automation system 185. In one embodiment, the interface between the wristband 110 and the smart phone 120 or other computer system 170 may be through an audio jack interface. In one embodiment, the interface may be through a BLUETOOTH™ or other personal area network interface.

In one embodiment, the sensing system 100 may further communicate with a network 160. Network 160 may include one or more of a wireless network (WiFi), cellular network, a local area network, a personal area network (PAN) such as BLUETOOTH™, or another type of wired or wireless connection. The network 160 may provide access to a computer system 170, remote server 180, home environmental controls 175, home automation system 185, and/or data on various third party systems 190. The computer system 170 may provide additional processing, and may, in one embodiment, provide the user with an additional user interface features. In one embodiment, the computer system 170 may be coupled directly to the sleep sensing system 110, continuously or periodically, via direct connection 175. This could be implemented, in one embodiment, via a Universal Serial Bus (USB), micro-USB, audio input based interface, or other type of wired connection. Alternatively, the sensor system and the computer system 170 may be coupled via network 160.

In one embodiment, server 180 may provide data to the sleep sensing system 100. In one embodiment, the sleep sensing system 100 may also provide information to the server 180. In one embodiment, the server 180 may collect data from multiple users, and use cumulative information to provide predictive recommendations, set default options, and suggest alterations to settings.

In one embodiment, the server 180 may also provide sound files to the sleeps sensing system 100, enabling updates to the music or other sounds being used. This may be done in response to a user request, in response to additional information being learned, in response to new research, or for other reasons. In one embodiment, the server 180 may be used to stream the sounds played to the sensing system.

In one embodiment, the sleep sensing system 100 may also couple via network 160 to third party systems 190 and/or home environmental controls 175. Third party systems 190 and/or home environmental controls 175 may provide environmental data to the sleep sensing system 100. Third party systems 190 may provide external environmental data, while home environmental controls 175 provide data, and in one embodiment enable control of, internal environment. Third party systems 190 may also provide sounds to the sleep sensing system 100. In one embodiment, the system may be set up to enable a user to download music or other appropriate sound sets from a store, such as the ITUNES MUSIC STORE™ by APPLE COMPUTERS™. In one embodiment, the sleep sensing system 100 couples to computer 170 or server 180, which in turn is coupled to third party systems. In this way, the sleep sensing system 100 can obtain data from third parties, without having to manage third party connections.

Figure 2:
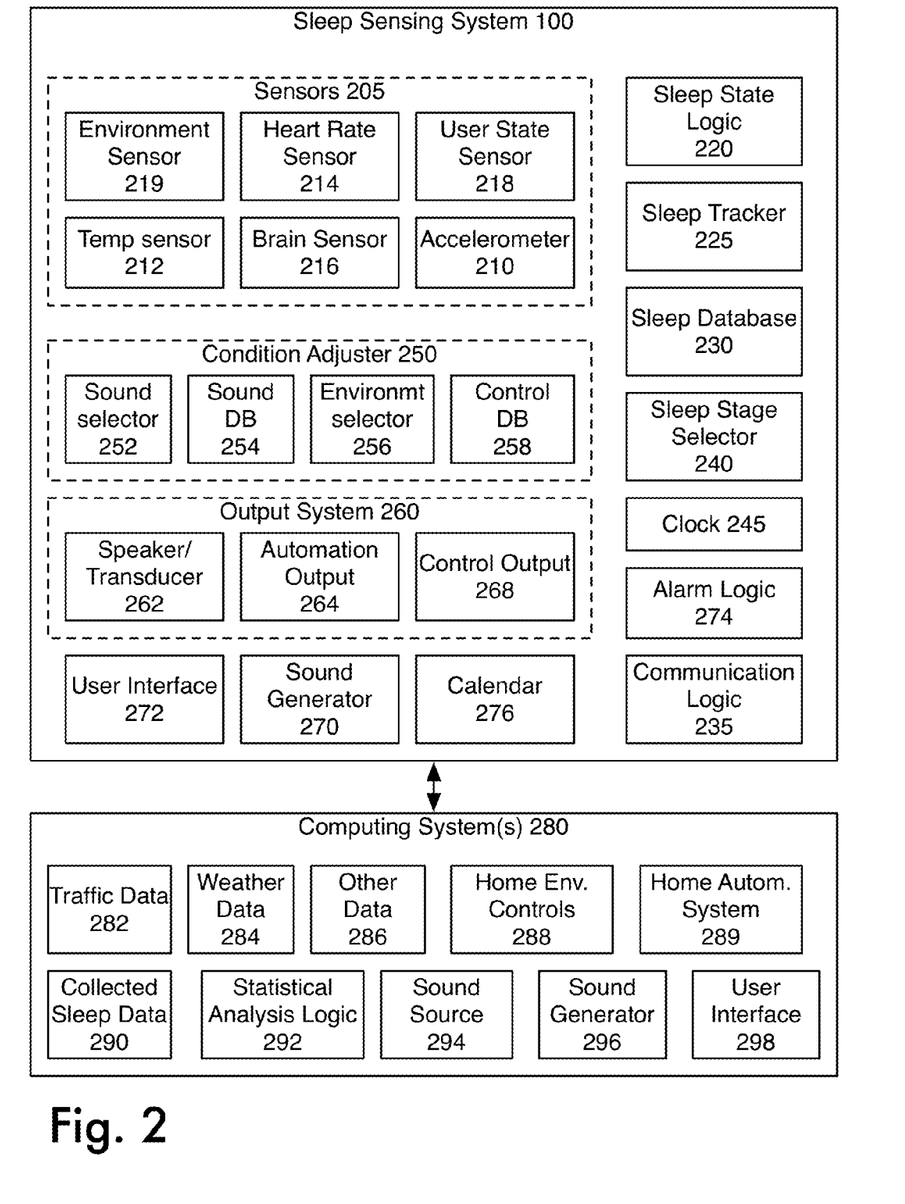
FIG. 2 is a block diagram of one embodiment of the system.

FIG. 2 is a block diagram of one embodiment of the system, including a sleep sensing system 100 and computing system 280, to which the sensing system 100 may be coupled using a wired connection or via a network connection. In one embodiment, the computing system 280 may be a local personal computer, a local server computer, or a remote server system, or a remote accessible website or other source of data.

The sleep sensing system 100 includes one or more sensors 205. The sensors 205 may include an accelerometer 210, a temperature sensor 212, a heart rate sensor 214. In one embodiment, temperature sensor 212 may include two sensors, one for the user's body temperature and the other for ambient temperature sensing. In one embodiment, sensors that detect brain waves 216 may also be used. In one embodiment, brainwave sensors, cameras to observe eye movement, or other sensors 218 may also monitor the user's state. Additional sensors to monitor the user's state 218, and/or the user's environment 219 may also be part of the sleep sensing system 100.

Sleep sensing system 100 further includes sleep state logic 220. Sleep state logic 220 utilizes data from one or more sensors 205, to determine the user's current sleep state. In one embodiment, the sleep state may be N1, N2, N3, and REM. In another embodiment, the sleep state may be light sleep, deep sleep, and REM sleep. In one embodiment, the sleep is grouped into light sleep and deep sleep, and awake. Other groupings of sleep state, including further divisions, or subdivisions, may also be used. In one embodiment, sleep state can be determined by sleep state logic 220 based on the user's micro-movements, body temperature, heart rate, and/or brain waves. Additional sensor data may be used to correctly identify the current sleep state of the user.

Sleep tracker 225 receives the current sleep state information from sleep state logic 220 and tracks the overall sleep for the present sleep period. Sleep tracker 225 in one embodiment adds the data for the current sleep period to a sleep database 230. The sleep database 230 tracks cumulative sleep information. In one embodiment, the information in the sleep database 230 may be used for predictive modeling for the user. The cumulative sleep data 290, collected on a computer system 280, from multiple users may be used for predictive modeling based on statistical analysis 292 for all users as well. In one embodiment, the data from sleep database 225 may be passed to computer system 280 using communication logic 235, to be used in the collected sleep data 290.

The data from sleep tracker 225 and sleep state logic 220 is used by the sleep stage selector 240, to select the optimal next sleep state for the user. In one embodiment, the sleep stage selector 240 also utilizes data from clock 245 and alarm logic 274.

In one embodiment, data from environment sensor 219 may also be used by sleep stage selector 240. In one embodiment, instead of an environment sensor 219, in sensors 205, the environment data may be received from a remote device, such as home environment controls 288, or home automation system 289. In one embodiment, data from computing system(s) 280 may also be used by the sleep stage selector 240. The external data may include traffic data 282, weather data 284, data from home environment controls 288, home automation system 289, and/or other data 286 that may influence the user's sleep quality and the time the user needs to awaken.

The optimal next sleep state, as selected by sleep state selector 240 is passed to the condition adjuster 250. In one embodiment, the optimal next sleep state may be the same state as the current sleep state. Condition adjuster 250 optionally selects one or more conditions to adjust. For example, sound selector 252 may select a sound from sound database 254, or use sound generator 270 to select the appropriate sound(s), to either maintain the user in their current sleep state, or transition them to the appropriate optimal next sleep stage. In one embodiment, sound selector 252 may access a remote sound source 294 through computer system 280. In one embodiment, sound selector 252 may receive sounds from sound generator 296.

Condition adjuster 250 may select, additionally or alternatively, one or more environmental variables to adjust using environment selector 256. The environmental variables may include temperature, light, humidity, mattress firmness, scents/smells, tactile feedback, etc. In one embodiment, one or more of these environmental variables may be adjusted via home environment controls 288 and/or home automation system 289.

In one embodiment, the condition adjuster 250 is only used when the user is not naturally transitioning to the optimal next sleep state. Thus, the system allows the user to move naturally through the sleep states, unless the system determines that the state to which the user would be moving is not optimal. In that case, the condition adjuster 250 may be used to guide the user to the pre-identified optimal sleep state.

In one embodiment, the user may enter condition preferences through user interface 265, or via a user interface 298 on computing system 280. The computing system 280 may be a local computer, a remote server, or remote computer system. In one embodiment, the user interface 298 may be presented via an application running on the sleep sending system 100 or computer system 280, or a web-based interface, or another type of interface. In one embodiment, the system includes one or more default sets of conditions for each sleep state and sleep state transition. In one embodiment, these default sets may be altered by the user, within certain parameters. For example, in one embodiment, transition to the awake state may be energizing music, the scent of coffee, and an increase in ambient light by default. If a user prefers something less energetic, or prefers not to have coffee, he or she may alter this setting. Similarly, the user may prefer the sounds of the rainforest rather than the sounds of the ocean, for transitioning into sleep.

When there is a condition adjustment selected by condition adjuster 250, it is sent to output system 260. Output system 260 may include one or more of a speaker/transducer 262 implemented as a separate device, in the same device, or headset. Output system 260 may also include automation output 264, to second information to home automation system 289 and/or control output 268 to adjust home environmental controls 288, or other output mechanisms to enable one or more conditions to be altered. In one embodiment, a sound may be conveyed via bone conduction or other means that does not involve traditional sound output. In one embodiment, the sound selector 252 may adjust the selected sounds, based on the type of sound output system 262 which is used. For example, bone conduction makes tones sound lower and fuller, thus a different selection may be preferred, or the selection's tone may be altered.

The other control output 268 may be haptic output, such as vibrations for example. In one embodiment, the other control output 268 may include scents. Other mechanisms, now known or later developed, to move the user between sleep phases may be utilized as part of output system 260.

Alarm logic 274, in one embodiment, optionally receives an alarm time from a user, via a user interface 265, 298. In one embodiment, the alarm logic 274 and the sleep stage selector 240 ensure that the user is woken up from an optimal sleep state. Waking up from a light sleep, rather than a deeper sleep, leads to the person feeling more awake, and less tired.

In one embodiment, the alarm logic 274 may interface to a calendar 275, to select a waking time based on calendared events. For example, if the user has a telephone conference scheduled at 7 a.m. the alarm logic 270 may set the alarm at 6:30 a.m. to ensure that the user can attend the scheduled telephone conference. In one embodiment, the system lets the user set a "nearest light sleep phase to Time" type of alarm. In one embodiment, the system lets the user set a particular time for the alarm, and ensures that the sleep states prior to that time enable the user to be in the optimal sleep state when the alarm is scheduled to go off.

Alarm logic 274, and user interface 265, 298 in one embodiment enable a user to select the alarm tones used. In one embodiment, the default alarm includes a sleep report. In one embodiment, the alarm initially is a set of tones designed to wake up and energize the user, followed by the sleep report. The sleep report, in one embodiment is an announcement of the user's completed sleep period data. For example, the announcement may be "Your optimal wake-up time is now. You slept 6.25 hours, with 4 hours of deep sleep, 2.1 hours of REM sleep, and it took you 17 minutes to fall asleep. Your sleep efficiency is 97%, and you are getting 95% of your optimal sleep." Additional data, including week-to-date data, or less data, may be provided.

In one embodiment, the system may further make a control announcement regarding adjusting the preferences via the user interface. For example, the message may continue "Press once to snooze, twice to dismiss, 3 times to push you wake up time forward by [26] minutes." In one embodiment, the length that the wake-up time is pushed forward is set based on sleep data. In one embodiment, the timing may be determined by the system to provide an optimal amount of additional rest. For example, the additional sleep segment may be 26 minutes as a default. This is the approximate time for a power nap, sufficient time to experience REM sleep, but not enough to go into a deep sleep. In one embodiment, the actual timing of the fraction of the sleep cycle selected is based on the user's own statistically analyzed sleep patterns.

In one embodiment, a sound of the alarm may be selected from available alarm tones. In one embodiment, this may be implemented as a ring tone. In one embodiment, the alarm may alternatively be a non-auditory alarm, such as a vibration, scent, or other mechanism. Such a silent alarm works because the alarm is played when the user is already in a light sleep phase.

Figure 3:
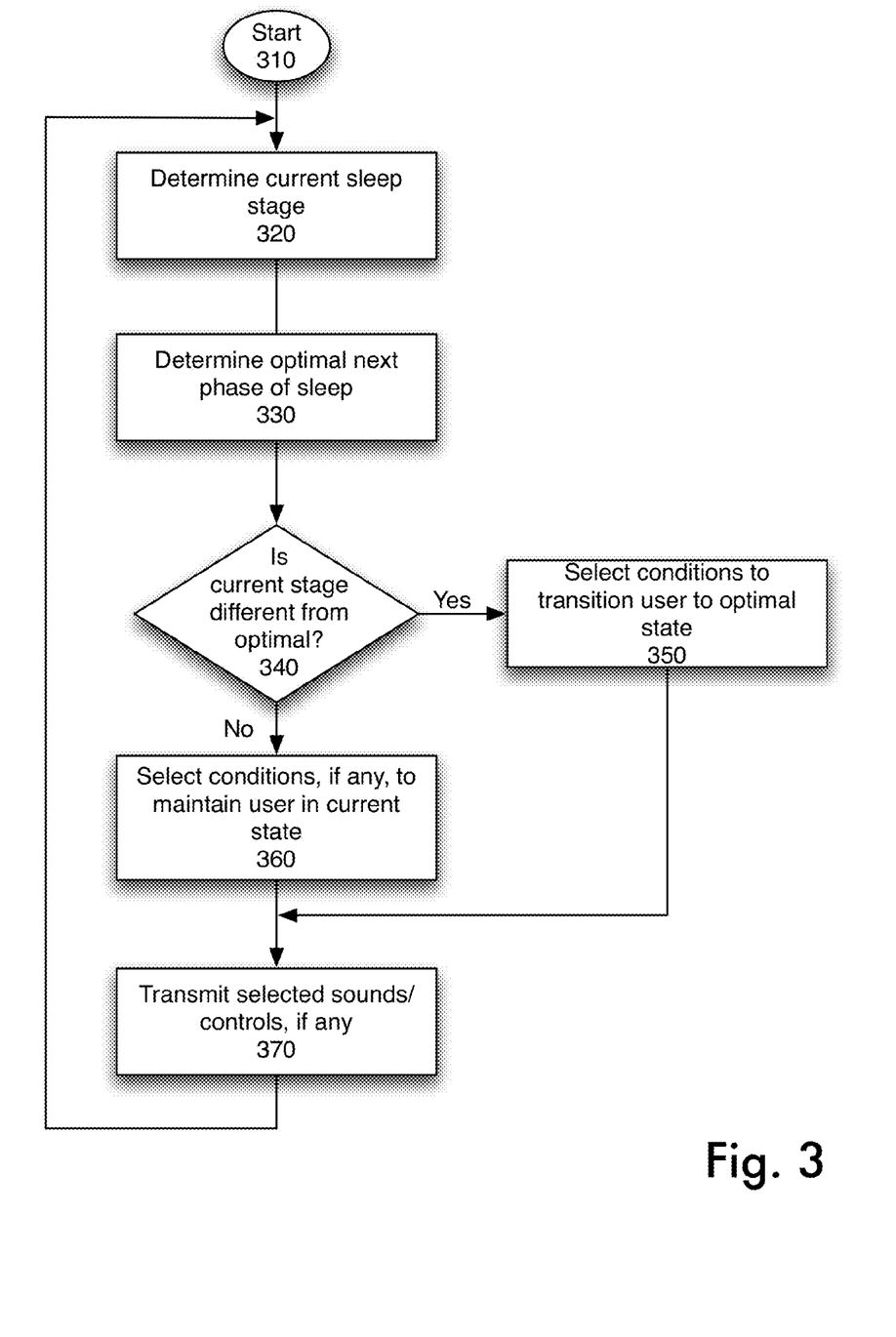
FIG. 3 is an overview flowchart of one embodiment of using the sleep system.

FIG. 3 is an overview flowchart of one embodiment of using the sleep system. The process starts at block 310. In one embodiment, this process starts whenever a user's sleep is initiated. In one embodiment, the process is initiated manually by a user, by selecting a "sleep setting," putting on and/or turning on the sleep sensor, or otherwise indicating an intention to sleep. In another embodiment, the process may be initiated automatically when the system detects that the user is falling asleep. In another embodiment, the process may be initiated automatically when the system detects that the user has lain down, and the timing indicates that this is likely done in order to sleep.

At block 320, the process determines the current sleep state of the user. In one embodiment, this is done by utilizing the data from one or more sensors. As noted above, sensors may include accelerometers, thermometers, blood pressure meters, heart rate sensors, or other sensors.

At block 330, the process determines the optimal next stage of sleep for the user. In one embodiment, this depends on the current time (e.g. 2 a.m.), the expected waking time of the user (e.g., 7 a.m.), and the sleep pattern so far in the current sleep period. In general, a user needs a certain amount of REM sleep for dreaming. However, deeper sleep is more restful. Furthermore, waking up from a light sleep leaves one more rested than waking up from a deeper sleep. Therefore, the current optimal stage of sleep may vary based on numerous factors. Other factors may also be taken into account, as will be described below.

Generally sleep is cyclical, a sleeper cycles through light sleep, REM sleep, and deep sleep multiple times in a sleep period. For the purposes of this description a "sleep period" is the entire night or other sleep unit, while a sleep cycle is a full cycle of light sleep, REM sleep, and deep sleep, which usually is about three hours for the average sleeper.

At block 340, the process determines whether the current sleep stage is different from the optimal next sleep stage. If so, at block 350, the process determines which conditions, if any, should be transmitted in order to move the user to the optimal next stage of sleep.

If the current sleep stage is the optimal next sleep stage, the process at block 360 determines which conditions, if any, should be selected to maintain the user in the optimal stage of sleep. In one embodiment, conditions are selected to maintain the user in the current stage of sleep if the data indicates that the user may otherwise leave this stage of sleep.

At block 370, the selected conditions are implemented. These conditions may include sounds, scents, vibrations, light/visual effects, temperature, humidity, mattress condition, and/or other types of output that may impact the user's sleep. The term "sound" is used to indicate the sensation produced by stimulation of the organs of hearing by vibrations transmitted through the air or other medium. These sounds may be music, tones, soundscapes of nature or water, sounds below the threshold of hearing, vibrations, binaural beats, etc.

The process then returns to block 320, to determine the user's current state of sleep. In one embodiment, the system periodically tests the user's sleep state, e.g. every few minutes. In another embodiment, the system continuously tests the user's sleep state. In another embodiment, the system utilizes one sensor to trigger testing of the sleep state. For example, the system may continuously measure body temperature, and when a change in body temperature indicates a change in sleep state, the other sensors may be used. In another example, the system may continuously or frequently test movement, and turn on other sensors to verify sleep state when needed. In one embodiment, the process periodically evaluates the optimal next stage of sleep, e.g. every few minutes, or every 30 minutes.

In one embodiment, when determining the next optimal phase of sleep, the system may also evaluate an estimated length of that sleep phase. If that determination is made, the system in one embodiment reduces the frequency of testing the current sleep state and the next optimal sleep state, during most of the estimated length of the sleep phase. For example, in one embodiment, if the next optimal sleep phase is determined to be deep sleep for the next 50 minutes, the system tests frequently until the user is determined to be in the deep sleep phase, which may take 2-5 minutes. Then, the system tests only every 10 minutes for the next 40 minutes, as long as the user remains in the deep sleep phase during that time. When the estimated end of the deep sleep phase is approaching, the system starts testing more frequently again.

Figure 4:
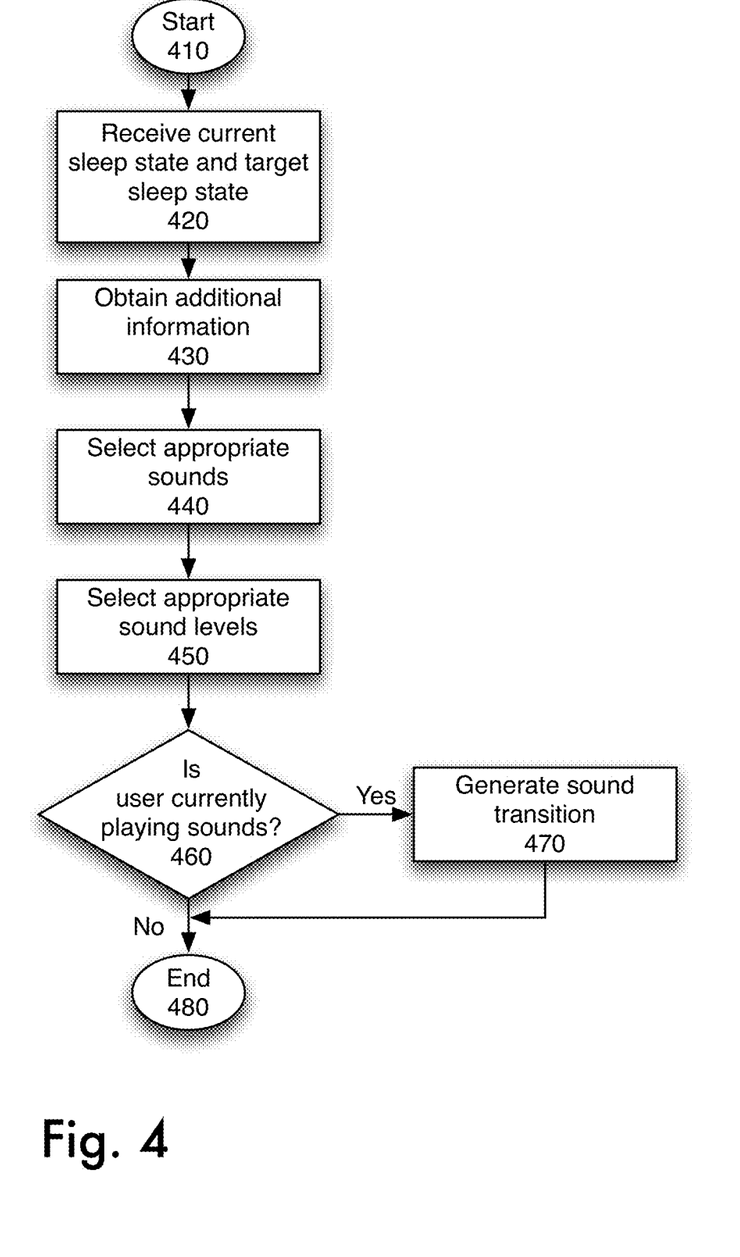
FIG. 4 is a flowchart of one embodiment of guiding the user into a correct sleep phase.

FIG. 4 is a flowchart of one embodiment of guiding the user into an optimal sleep phase, using sounds. It would be understood by one of skill in the art that similar processes may be used for other adjustable conditions, such as scents, temperatures, etc. The process starts at block 410. In one embodiment, this flowchart corresponds to block 350 of FIG. 3.

Figure 5:
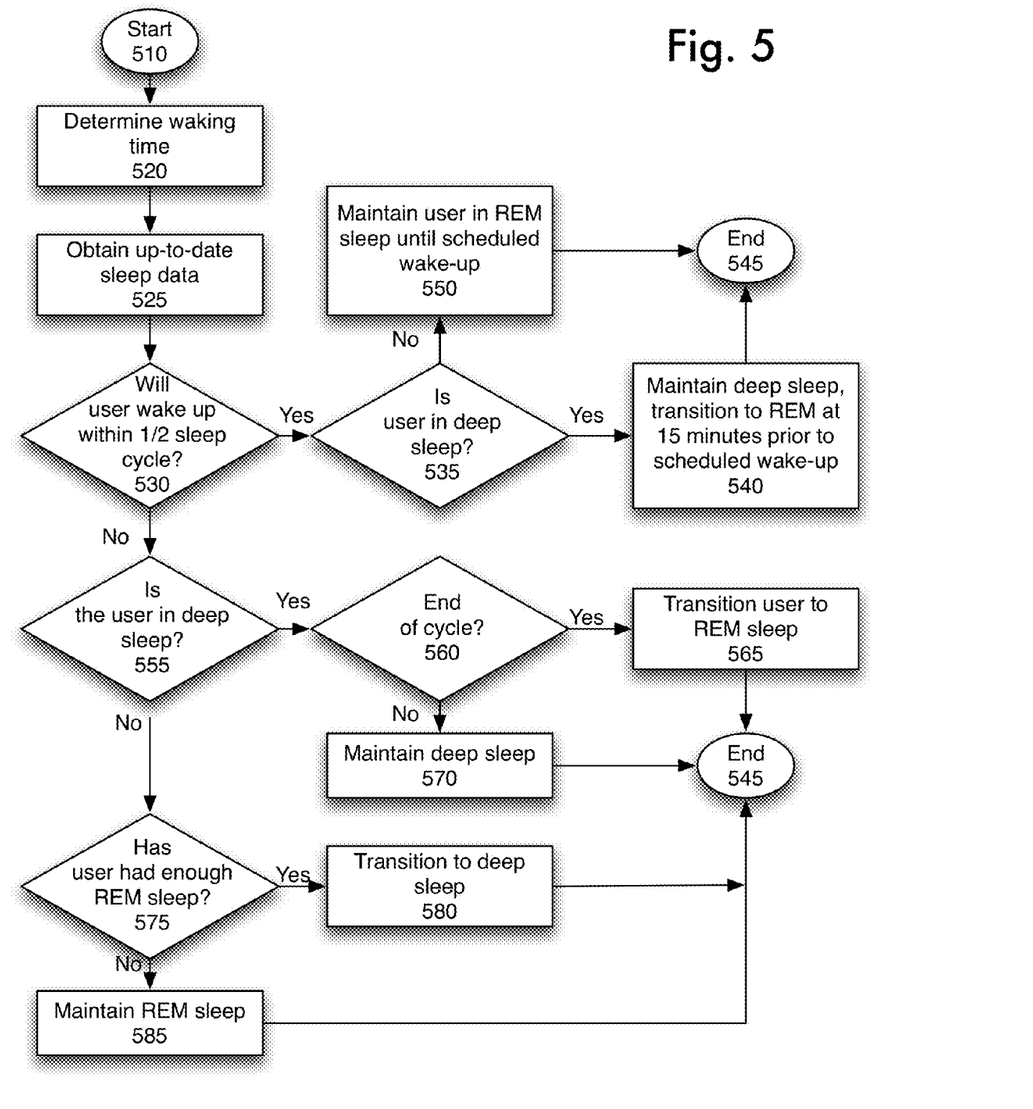
FIG. 5 is a flowchart of one embodiment of determining the optimal sleep state.

At block 420, the process receives the current sleep state and the target sleep phase. The target sleep stage is the optimal next sleep phase. FIG. 5 is a flowchart of one embodiment of determining the optimal next sleep phase.

At block 430, the process determines additional available information about the user, and the environment when appropriate. The information about the user may include data from one or more sensors, as well as user personal data, e.g. age, sex, etc. Environmental data may include ambient temperature data, humidity, noise level, and other information that may impact the user's quality of sleep or sound effectiveness.

At block 440, the appropriate sounds are selected. The appropriate sound has a cadence and tone that is designed to guide the sleeper into the optimal sleep phase. For example, it is known that music with a slower cadence slows down the heart rate.

In one embodiment, brainwave entrainment can be used to guide a user to various sleep states. The sounds selected may use binaural beat, monaural beats, isochronic tones, or other modes of modulation that can guide the brain into the optimal sleep state.

In one embodiment, the sound type may be based on user preferences, entered through a user interface. For example, the user may indicate that he or she has a preference for nature sounds. In that case, the appropriate nature sounds would be selected. In one embodiment, jazz, pop, classical, or other musical genres may be set as a preference. In one embodiment, the system uses generated sounds in order to have precise control of the tones and beats used. In one embodiment, the system may utilize existing musical compositions, either as is or with modifications to assist in guiding a user into the optimal sleep state.

At block 450, the system in one embodiment selects an appropriate sound volume for the selected sound. The selected sound volume is based on a combination of the user's current sleep state and environmental factors. In a louder environment, the sound is played more loudly.

At block 460, the process determines whether the system is currently playing sounds. If so, at block 470, a transition is created, to gently transition from the current sounds to the appropriate selected sounds.

The process then ends at block 480. A similar flow, in one embodiment, can be used for selecting a sound to maintain the user in a particular sleep state.

FIG. 5 is a flowchart of one embodiment of determining the next optimal sleep phase. The next optimal sleep state depends on a number of factors. The process starts at block 510. In one embodiment, this flowchart corresponds to block 330, in FIG. 3.

At block 520, the process determines the expected time the user must wake up. In one embodiment, this calculation is done once per sleep period. Subsequent calculations of the appropriate sleep phase use the previously calculated waking time.

In one embodiment, if there is an alarm function available in the system, and the alarm is set, the alarm time is used as the waking time. In one embodiment, if no alarm is set, the system may interface with a user's calendar, and appointments in the calendar may be used as the basis for setting the waking time. In one embodiment, if the determination is based on an appointment in the calendar, the system may perform further calculations to provide sufficient time for a user to reach the destination. For example, if the user has on their calendar "Meeting at FullPower, Inc." the system may wake the user in time to allow the user to get ready, and go to the scheduled meeting. In one embodiment, such calculations may take into account the weather. In one embodiment, such calculations may also take into account the user's general modes of transportation, if this information is available.

In one embodiment, if there is no other setting, the optimal sleep length of the user is set as the waking time. For example, the average 15-year old should sleep for 9 hours. Thus, in one embodiment, the system is set to wake such a user after 9 hours of sleep. In one embodiment, the optimal sleep length may be adjusted based on the user's personal characteristics, or additional data about the user. For example, if the user has indicated that he or she feels most rested after an 8-hour sleep, that may be used.

In one embodiment, if the user did not set an alarm, either directly or via the calendar, the system may not set an alarm and may let the user sleep as long as he or she can.

At block 525, the sleep data about the current sleep period so far is collected. The sleep data includes the number and length of each sleep phase in this sleep period.

There are three states of non-REM sleep: Stage N1 (Transition to sleep), Stage N2 (Light sleep), and Stage N3 (Deep sleep). The N1 stage is short, lasting only a few minutes, while stage N2 is the first stage of true sleep lasting about half an hour. The N3 stage is deep sleep, from which it is hard to wake. REM sleep is where dreaming occurs.

The average adult spends approximately fifty percent of total sleep time in stage N2, twenty percent in REM sleep, and thirty percent in the remaining stages, including deep sleep. Deep sleep renews the body, and is important for health, and REM sleep is necessary for the mind. While sleep needs vary from individual to individual, everyone needs an adequate amount of REM sleep and deep sleep.

Sleep generally occurs in cycles, which take on average 90 minutes. The precise length of the cycle depends on the individual as well as environmental factors. During each cycle, the user should get some deep sleep and some REM sleep. Optimally most of the sleep in any sleep period should be either REM or deep sleep. The current sleep phase and the cumulative sleep phases so far are used to calculate the optimal next sleep phase.

At block 530, the process determines whether the user should be waking up in less than a half sleep cycle. As noted above, a full sleep cycle is generally 90 minutes. However, the sleep cycle length varies by person, and in one embodiment, the system may adjust the default sleep cycle length by observed sleep cycle length for the particular user.

If the user should be waking up within half a sleep cycle, the system continues to block 535, where the process determines whether the user is in deep sleep. If the user is in deep sleep, at block 540, the process sets the optimal sleep phase to maintaining the user in deep sleep until approximately 15 minutes prior to the scheduled waking period. Approximately 15 minutes prior to the waking period, the system should shift the user into REM sleep. By waking up from the REM sleep, rather than deep sleep, the user will wake up more refreshed and rested, and have more energy. In one embodiment, the length of time needed to shift the user from deep sleep into REM sleep is user dependent, therefore this time frame may be adjusted, as needed. The process then ends at block 545.

If the user is not in deep sleep, the system at block 550 sets REM sleep as the optimal sleep state. In general, 45 minutes is too short to transition into deep sleep, have a sufficiently long deep sleep cycle, and transition back into REM sleep prior to waking. Therefore, the system sets as the optimal sleep state the REM state. The user can be maintained in the REM sleep state, which will enable them to awaken well rested. The process then ends at block 545.

If, at block 530, the process determines that the user does not need to wake in less than a half sleep cycle, the process continues to block 555.

At block 555, the process determines whether the user is in deep sleep. If so, at block 560, the process determines whether it is the end of a natural sleep cycle. In general, the system is designed not to disrupt the cyclic nature of sleep, but rather to optimize the sleep quality by adjusting the sleep. Therefore, if it is the end of the cycle, at block 565 the optimal next sleep phase is set to a transition to REM sleep. The process the ends at block 545.

If it is not the end of a sleep cycle, the optimal sleep stage is set to maintaining the deep sleep, at block 570. The process then ends at block 545.

If the user is not in deep sleep, at block 575 the process determines whether the user has had enough REM sleep. In general, the REM stage of sleep can be shortened without impacting the user, as long as the user gets more than a minimum required amount of REM sleep. In one embodiment, the minimum amount of REM sleep that allows a user to stay healthy and refreshed is 30 minutes per cycle. In one embodiment, this is user dependent, and the system may use data obtained during unmodified natural sleep cycles to set the REM sleep minimum for the user. If the user has not yet had enough REM sleep, the optimal next sleep stage at block 585 is set to maintain the user in the REM state. If the user has had enough REM sleep, at block 580 the process sets the optimal stage as a transition to deep sleep. The process then ends at block 545.

In this way, the system attempts to enable a user to have more refreshing sleep period, by ensuring that the user gets as much deep sleep as possible, while getting sufficient REM sleep.

The timings described in FIG. 5 are merely exemplary. One of skill in the art would understand that these settings may be altered, for individual users as well as for all users. In a different embodiment, it is possible that the system would add a necessary level of light sleep as well. Furthermore, if additional sleep phases, or needs, are indicated or discovered, each may be modulated by this system.

Figure 6A:
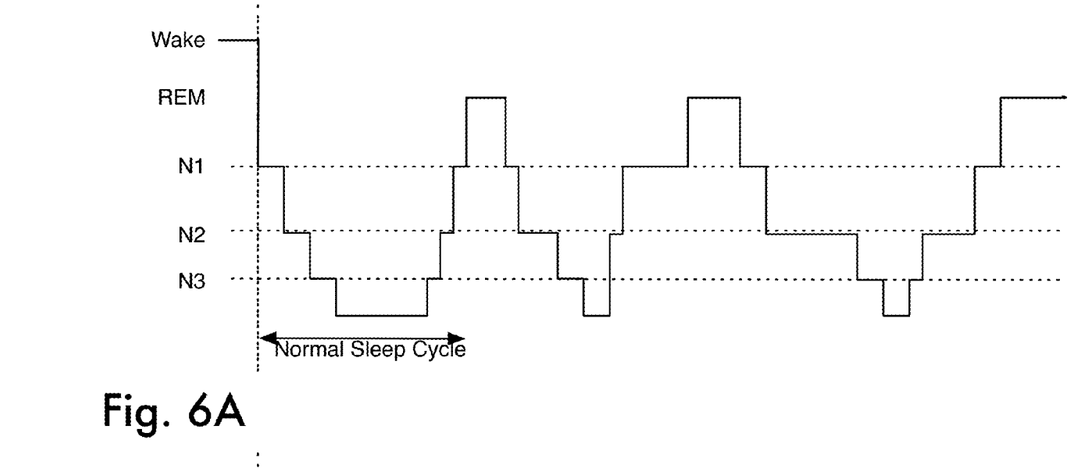
FIGS. 6A and 6B show a difference between an exemplary normal sleep period shown by FIG. 6A and an optimized sleep period shown by FIG. 6B.
Figure 6B:
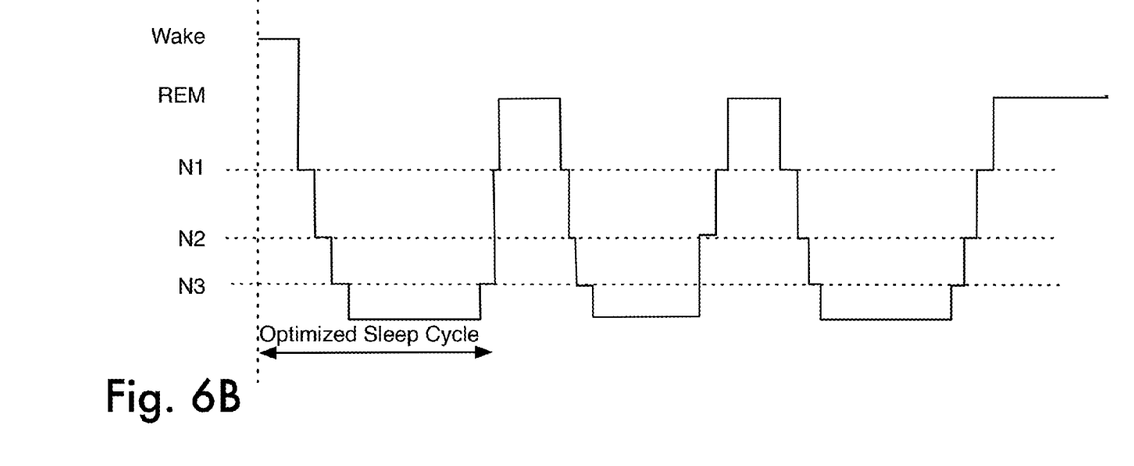

FIGS. 6A and 6B show a difference between an exemplary normal sleep cycle shown by FIG. 6A and an optimized sleep cycle shown by FIG. 6B. As can be seen, although the sleep cycles are generally maintained at the same approximate length, in the optimized sleep cycle the user gets more deep sleep and more REM sleep. This provides better rest, and improves sleep quality.

Figure 7:
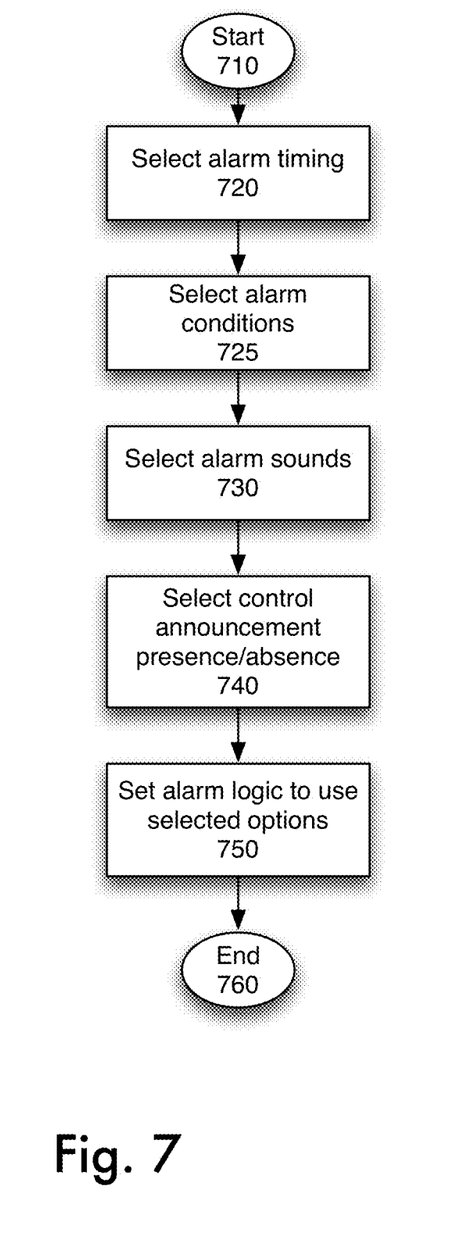
FIG. 7 is a flowchart of one embodiment of selecting an alarm to terminate the sleep period.

FIG. 7 is a flowchart of one embodiment of choosing the alarm for waking the user. The process starts at block 710. As noted above, the system calculates the appropriate time to sound an alarm. The actual alarm may include sounds, vibrations, scents, tactile changes, alterations of the light, and other conditions are selected in accordance with this flowchart, in one embodiment. The process, in one embodiment, occurs when the alarm function is first initiated, or when the user alters any settings associated with the alarm.

The process starts at block 510.

At block 720, the system prompts the user to select alarm timing. In one embodiment, the alarm timing may be an exact time, e.g. 7:25 a.m., or a "nearest optimal time," e.g. prior to 7:30 a.m.

At block 725, the system prompts the user to select the alarm conditions. Alarm conditions that may be adjusted depend on the controls available to the system. For example, if the user has a coffee machine that is connected to the alarm system, the coffee machine may be initiated to add the scent of coffee. A scent generation system may alternatively be used to generate a scent. Additional controls may include temperature, mattress firmness, light levels, humidity, and other aspects of the user's personal environment.

At block 730, the user can select alarm sounds. In one embodiment, in addition to the "standard" alarm sounds available, the user may be presented with additional options. Additional options, in one embodiment include "sleep reporting" and "silent." A silent alarm would use the other conditions, such a vibration or other non-sound-based alert. In one embodiment, a "silent" alarm may also indicate that the alarm be personal. A personal alarm is designed not to wake any other sleepers, thus excluding alarm options such as increasing light levels in the room, or significantly altering the room temperature. The sleep reporting alarm is designed to announce information about the user's just completed sleep period. In one embodiment, this information is available throughout the day, as well.

At block 740, the process permits the user to select whether control announcement should be provided along with the alarm. In one embodiment, for any non-silent alarm a control announcement may be added to the alarm. The control announcement informs the user how to alter the alarm settings simply. In one embodiment, the control announcement may be, "Press once to snooze, press twice to dismiss, press three times for additional sleep time of 26 minutes." In one embodiment, this announcement is included by default with the sleep reporting alarm, and may also be added to the other alarm formats that are non-silent.

At block 750, the process sets the alarm logic to use the selected alarm format. In one embodiment, regardless of whether the sleep reporting alarm format is used, the sleep reporting is available to the user via the user interface. In one embodiment, for example, the user may press a button, or otherwise issue a command to provide the sleep report.

The process ends at block 760.

Figure 8:
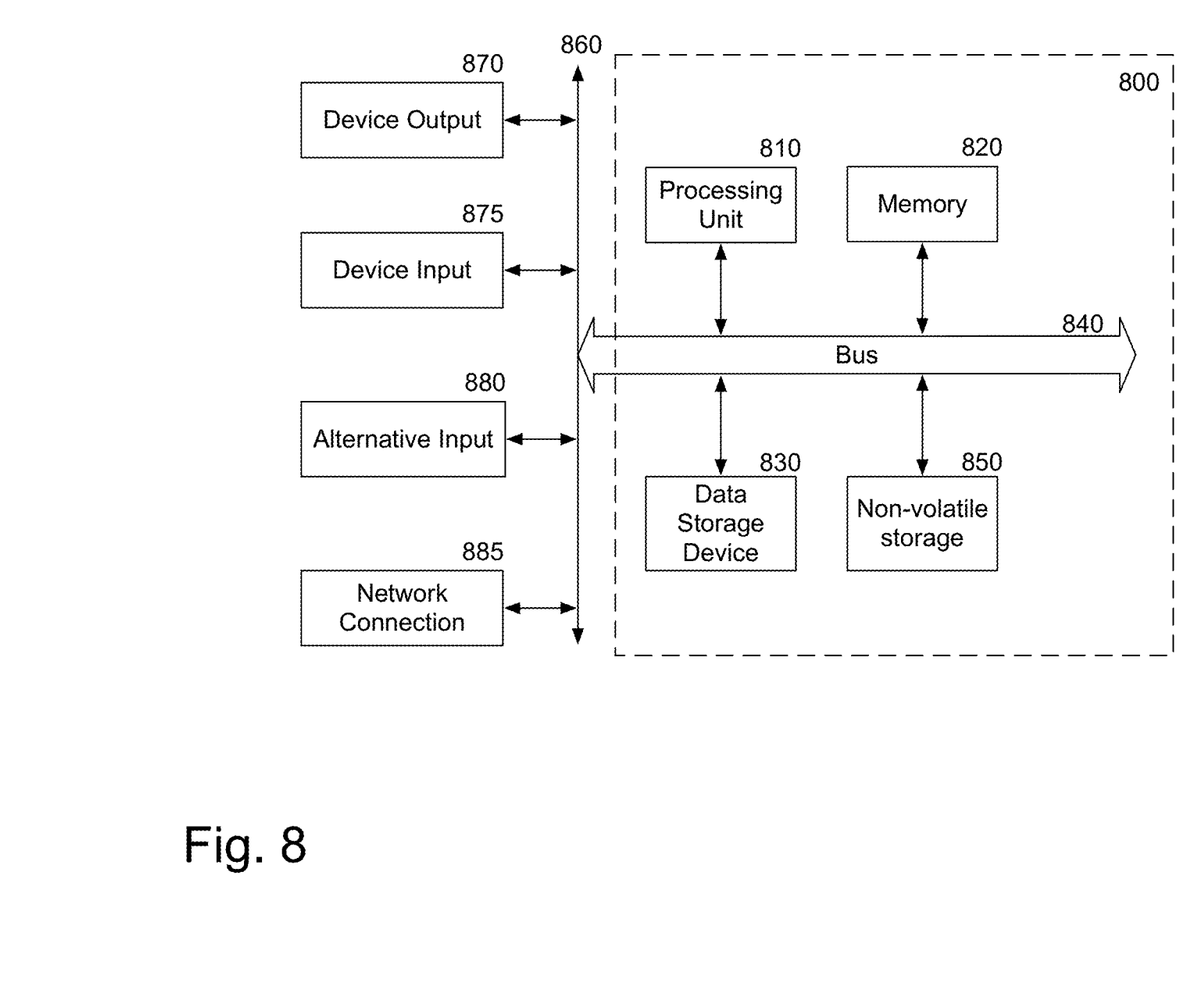
FIG. 8 is a block diagram of a computer system that may be used in the present invention.

FIG. 8 is a block diagram of a particular machine that may be used with the present invention. It will be apparent to those of ordinary skill in the art, however that other alternative systems of various system architectures may also be used.

The data processing system illustrated in FIG. 8 includes a bus or other internal communication means 840 for communicating information, and a processing unit 810 coupled to the bus 840 for processing information. The processing unit 810 may be a central processing unit (CPU), a digital signal processor (DSP), or another type of processing unit 810.

The system further includes, in one embodiment, a random access memory (RAM) or other volatile storage device 820 (referred to as memory), coupled to bus 840 for storing information and instructions to be executed by processor 810. Main memory 820 may also be used for storing temporary variables or other intermediate information during execution of instructions by processing unit 810.

The system also comprises in one embodiment a read only memory (ROM) 850 and/or static storage device 850 coupled to bus 840 for storing static information and instructions for processor 810. In one embodiment the system also includes a data storage device 830 such as a magnetic disk or optical disk and its corresponding disk drive, or Flash memory or other storage which is capable of storing data when no power is supplied to the system. Data storage device 830 in one embodiment is coupled to bus 840 for storing information and instructions.

The system may further be coupled to an output device 870, such as a cathode ray tube (CRT) or a liquid crystal display (LCD) coupled to bus 840 through bus 860 for outputting information. The output device 870 may be a visual output device, an audio output device, and/or tactile output device (e.g. vibrations, etc.)

An input device 875 may be coupled to the bus 860. The input device 875 may be an alphanumeric input device, such as a keyboard including alphanumeric and other keys, for enabling a user to communicate information and command selections to processing unit 810. An additional user input device 880 may further be included. One such user input device 880 is cursor control device 880, such as a mouse, a trackball, stylus, cursor direction keys, or touch screen, may be coupled to bus 840 through bus 860 for communicating direction information and command selections to processing unit 810, and for controlling movement on display device 870.

Another device, which may optionally be coupled to computer system 800, is a network device 885 for accessing other nodes of a distributed system via a network. The communication device 885 may include any of a number of commercially available networking peripheral devices such as those used for coupling to an Ethernet, token ring, Internet, or wide area network, personal area network, wireless network or other method of accessing other devices. The communication device 885 may further be a null-modem connection, or any other mechanism that provides connectivity between the computer system 800 and the outside world.

Note that any or all of the components of this system illustrated in FIG. 8 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 820, mass storage device 830, or other storage medium locally or remotely accessible to processor 810.

It will be apparent to those of ordinary skill in the art that the system, method, and process described herein can be implemented as software stored in main memory 820 or read only memory 850 and executed by processor 810. This control logic or software may also be resident on an article of manufacture comprising a computer readable medium having computer readable program code embodied therein and being readable by the mass storage device 830 and for causing the processor 810 to operate in accordance with the methods and teachings herein.

The present invention may also be embodied in a handheld or portable device containing a subset of the computer hardware components described above. For example, the handheld device may be configured to contain only the bus 840, the processor 810, and memory 850 and/or 820.

The handheld device may be configured to include a set of buttons or input signaling components with which a user may select from a set of available options. These could be considered input device #1 875 or input device #2 880. The handheld device may also be configured to include an output device 870 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 810, a data storage device 830, a bus 840, and memory 820, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 885.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 810. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A sleep sensing system comprising:
a sensor to obtain real-time information about a user during sleep;
a sleep state logic to determine the user's current sleep state based on the real-time information;
a sleep stage selector to select an optimal next sleep state for the user based on the current sleep state and an expected waking time for the user, where the optimal next sleep state is one of deep sleep, REM sleep, and light sleep prior to waking; and
a condition adjuster to select one or more conditions to adjust in the user's environment during the sleep to guide the user from the current sleep state to a deeper sleep state when the optimal next sleep state is identified as deep sleep, and to guide the user from the current sleep state to a lighter sleep state when the optimal next sleep state is identified as a lighter sleep state.

2. The sleep sensing system of claim 1, further comprising:
the sleep stage selector using data from a sleep tracker, indicating sleep state data for a current sleep period, to determine the optimal next sleep state for the user.

3. The sleep sensing system of claim 1, further comprising:
the sleep stage selector using data from a clock and an alarm logic to determine the optimal next sleep state for the user.

4. The sleep sensing system of claim 1, further comprising:
an output system to adjust one or more conditions to keep the user in the current sleep state, when the optimal next sleep state is the same as the current sleep state.

5. The sleep sensing system of claim 4, wherein the output system outputs sounds when the user's natural sleep phase needs to be shifted.

6. The sleep sensing system of claim 1, wherein the sensors comprise one or more of an accelerometer, a thermometer, a heart rate monitor, a brainwave monitor.

7. The sleep sensing system of claim 6, wherein the sensors further comprise one of: environmental sensor, an interface to home environment controls to receive environmental data, and an interface to a home automation system to receive environmental data.

8. The sleep sensing system of claim 1, wherein the sensor is implemented in one of: an armband, a mobile telephone, a wristband, a pillow, or a sleep mask.

9. The sleep sensing system of claim 1, wherein the condition is one or more of: sound, tactile output, light level, visual output, scent, temperature, humidity, and mattress firmness.

10. A method comprising:
determining a current sleep phase of a user based on real-time information;
determining an optimal next sleep phase for the user based on the current sleep state and an expected waking time for the user;
determining whether the user needs to be moved to the optimal next sleep phase, and when the user needs to be moved to the optimal next sleep phase, utilizing an output system to adjust one or more conditions in the user's environment during the sleep to guide the user to the optimal next sleep phase, wherein the optimal next sleep phase is one of a deep sleep, REM sleep, and light sleep prior to waking; and
guiding the user from the current sleep phase to a deeper sleep state when the optimal next sleep state is identified as deep sleep, and to a lighter sleep state when the optimal next sleep state is identified as a lighter sleep state.

11. The method of claim 1, wherein the condition is one or more of: sound, tactile output, light level, visual output, scent, temperature, humidity, and mattress firmness.

12. The method of claim 10, further comprising:
using data from a sleep tracker, indicating sleep state data for a current sleep period, to determine the optimal next sleep state for the user.

13. The method of claim 10, further comprising:
using data from a clock and an alarm logic to determine the optimal next sleep state for the user.

14. The method of claim 10, further comprising:
adjusting one or more conditions to keep the user in the current sleep state, when the optimal next sleep state is the same as the current sleep state.

15. The method of claim 10, further comprising:
sending commands to one of a home environment controller or a home automation system, to adjust the conditions.

16. The method of claim 15, further comprising:
receiving environmental data from the one of the home environment controller and the home automation system.

17. The method of claim 10, wherein the sensor is implemented in one of: an armband, a mobile telephone, a wristband, a pillow, or a sleep mask.

18. A sleep sensing system comprising:
a sleep sensor including one or more sensors to obtain real-time information about a user;
a processor to:
   determine the user's current sleep state based on the real-time information; and
   select an optimal next sleep state for the user based on the current sleep state and an expected waking time for the user; and
an output mechanism to adjust one or more conditions in the user's environment during the current sleep state to guide the user from the current sleep state to a deeper sleep state when the optimal next sleep state is identified as deep sleep, and to guide the user from the current sleep state to a lighter sleep state when the optimal next sleep state is identified as a lighter sleep state.

19. The sleep sensing system of claim 18, wherein the one or more conditions include one or more of: sound, tactile output, light level, visual output, scent, temperature, humidity, and mattress firmness.

20. The sleep sensing system of claim 18, wherein the optimal next phase of sleep is determined based on a combination of one or more of: sleep state data for the current sleep period and an estimated waking time, the estimated waking time based on one or more of: an alarm and a calendar entry.

* * * * *